(12) United States Patent
Schmitt (10) Patent No.: US 11,872,123 B2
(45) Date of Patent: Jan. 16, 2024

(54) METHOD FOR MANUFACTURING A CARDIAC VALVE PROSTHESIS

(71) Applicant: GrOwnValve GmbH, Berlin (DE)

(72) Inventor: Boris Schmitt, Berlin (DE)

(73) Assignee: GROWNVALVE GMBH, Berlin (DE)

( * ) Notice: Subject to any disclaimer, the term of this patent is extended or adjusted under 35 U.S.C. 154(b) by 277 days.

(21) Appl. No.: 17/118,246

(22) Filed: Dec. 10, 2020

(65) Prior Publication Data
US 2022/0183826 A1    Jun. 16, 2022

(51) Int. Cl.
| | |
|---|---|
| *A61F 2/24* | (2006.01) |
| *A61L 27/36* | (2006.01) |
| *B33Y 80/00* | (2015.01) |
| *B33Y 10/00* | (2015.01) |

(52) U.S. Cl.
CPC .......... *A61F 2/2415* (2013.01); *A61F 2/2418* (2013.01); *A61F 2/2427* (2013.01); *A61L 27/3625* (2013.01); *A61L 27/3641* (2013.01); *A61F 2240/004* (2013.01); *A61L 2430/20* (2013.01); *B33Y 10/00* (2014.12); *B33Y 80/00* (2014.12)

(58) Field of Classification Search
CPC .... A61F 2/2415; A61F 2/2418; A61F 2/2427; A61F 2240/004; A61L 27/3625; A61L 27/3641; A61L 2430/20; B33Y 10/00; B33Y 80/00
See application file for complete search history.

(56) References Cited

U.S. PATENT DOCUMENTS

| | | | | | |
|---|---|---|---|---|---|
| 4,778,461 | A | * | 10/1988 | Pietsch | A61L 33/0005 623/2.19 |
| 5,163,953 | A | * | 11/1992 | Vince | A61F 2/2418 623/2.11 |
| 5,509,932 | A | * | 4/1996 | Keogh | A61L 27/28 623/23.72 |
| 5,824,063 | A | * | 10/1998 | Cox | A61L 27/3604 435/238 |

(Continued)

FOREIGN PATENT DOCUMENTS

| | | |
|---|---|---|
| WO | 2004047620 A2 | 6/2004 |
| WO | 2004113431 A1 | 12/2004 |

(Continued)

OTHER PUBLICATIONS

Antunes, P. et al., "Utilisation of Oleuropein as a crosslinking agent in collagenic films," ResearchGate Website, Available Online at https://www.researchgate.net/publication/235608241_Utilisation_of_oleuropein_as_crosslinking_agent_in_collagenic_films, Jan. 2008, 12 pages.

*Primary Examiner* — Suzette J Gherbi
(74) *Attorney, Agent, or Firm* — McCoy Russell LLP (57) ABSTRACT

A method for manufacturing a cardiac valve prosthesis is disclosed. This method comprises the following steps: a) shaping human or animal body tissue in a shaping process to give the body tissue a shape of a cardiac valve, and b) fixation and stabilization of the body tissue by a cross-linking agent, thereby preserving the shape given to the body tissue by the shaping process and thus obtaining a cardiac valve prosthesis. Furthermore, a method of implanting an autologous or allogenic cardiac valve prosthesis to an individual in need thereof is disclosed.

23 Claims, 5 Drawing Sheets

(56) References Cited

U.S. PATENT DOCUMENTS

| | | | |
|---|---|---|---|
| 6,328,763 B1* | 12/2001 | Love | A61F 2/2472 623/2.15 |
| 9,095,430 B2* | 8/2015 | Cunanan | A61L 27/507 |
| 9,492,230 B2* | 11/2016 | Schneider | B65B 55/18 |
| 10,987,449 B2* | 4/2021 | Sierad | A61L 27/3625 |
| 11,479,752 B2* | 10/2022 | Ekser | C12N 5/0688 |
| 2005/0187461 A1 | 8/2005 | Murphy et al. | |
| 2006/0259136 A1 | 11/2006 | Nguyen et al. | |
| 2007/0150052 A1 | 6/2007 | Santilli | |
| 2007/0208550 A1 | 9/2007 | Cao et al. | |
| 2008/0124373 A1* | 5/2008 | Xiao | A61L 31/026 623/1.42 |
| 2013/0110097 A1* | 5/2013 | Schneider | A61L 27/3604 606/14 |
| 2015/0005874 A1 | 1/2015 | Vidlund et al. | |
| 2015/0306277 A1* | 10/2015 | Pathak | A61P 21/02 424/443 |
| 2015/0335422 A1* | 11/2015 | Straka | A61F 2/2415 435/284.1 |
| 2015/0379231 A1 | 12/2015 | Singer | |
| 2016/0038251 A1 | 2/2016 | Grady et al. | |
| 2017/0057169 A1 | 3/2017 | Grbic et al. | |
| 2017/0100239 A1* | 4/2017 | Rzany | A61F 2/2415 |
| 2018/0174068 A1 | 6/2018 | Dahl et al. | |
| 2019/0151509 A1* | 5/2019 | Kheradvar | A61L 27/3826 |
| 2020/0237514 A1* | 7/2020 | Kofidis | A61F 2/2415 |
| 2021/0229362 A1* | 7/2021 | Kofidis | A61F 2/2418 |
| 2021/0236688 A1* | 8/2021 | Wagner | A61L 27/18 |
| 2022/0151765 A1* | 5/2022 | Qin | A61L 27/56 |
| 2022/0233306 A1* | 7/2022 | Yacoub | A61L 27/507 |
| 2022/0331488 A1* | 10/2022 | Ogle | B33Y 80/00 |
| 2022/0362022 A1* | 11/2022 | Dorff | A61F 2/2466 |

FOREIGN PATENT DOCUMENTS

| | | |
|---|---|---|
| WO | 2006115733 A2 | 11/2006 |
| WO | 2008079272 A2 | 7/2008 |
| WO | 2012068241 A2 | 5/2012 |
| WO | 2013028387 A2 | 2/2013 |
| WO | 2017042627 A1 | 3/2017 |
| WO | 2018108276 A1 | 6/2018 |

* cited by examiner

METHOD FOR MANUFACTURING A CARDIAC VALVE PROSTHESIS

TECHNICAL FIELD

The disclosure relates in general to cardiac valve replacement by biological cardiac valves prostheses.

BACKGROUND

Cardiac valve replacement using mechanical cardiac valves is established since the 1960s. Synthetically manufactured prostheses made from metal or plastic (polymers) are implanted to a patient in an open-heart surgery by use of cardiopulmonary bypass. The disadvantage of this procedure is the necessity of a lifelong anticoagulation therapy to avoid the formation of thrombi on the foreign surface of the prostheses. On the other hand, an advantage is the theoretic lifelong durability of the prosthetic cardiac valve. Therefore, it is mostly used for young adults. Female patients who want to give birth are mostly excluded from this therapy so far.

Biological cardiac valves are mostly produced from bovine or porcine pericardium or consist of whole bovine or porcine cardiac valves. In addition, bovine jugular vein valves are used as cardiac valve prostheses. Valves from animal tissue are called xenogenic. They either are implanted surgically or, since around year 2000, are implanted by cardiac catheter interventions as stented cardiac valves.

Further, biological cardiac valves can be harvested from human valve donors (allografts) or in some cases from the patient herself/himself for use as an autograft (e.g. in the so called ROSS procedure).

The advantage in using biological materials is avoidance of long-term anticoagulation therapy. The disadvantage, however, is that—apart from autografts—these cardiac valves are eventually rejected due to an immune reaction since they originate from a foreign source. This rejection often occurs even though a multistep pretreatment is performed to reduce the risk of an immune reaction. The result of such an immune reaction is degradation of the implanted cardiac valve. Therefore, the durability of biological cardiac valves—especially xenografts—is limited to approximately 5 to 15 years. Afterwards, another cardiac valve replacement is necessary.

The advantage of valves of human origin is a longer durability due to a lower immune response. The main disadvantage is, however, that these valves are increasingly difficult to obtain since the willingness for donations decreases. A special case is the self-donation: By an operation called ROSS procedure, the own (autologous) pulmonary valve is implanted instead of the diseased aortic valve, wherein the missing pulmonary valve is then replaced by a xeno- or allograft referred to above.

As already mentioned, cardiac valve prostheses can be implanted by a surgical or an interventional or a hybrid procedure (combining surgical and interventional techniques). A replacement by an interventional transcutaneous procedure is based on the use of catheters and the modified Seldinger technique. The intervention can be subdivided into a transvenous, transarterial, and a transapical intervention. The transapical access is established through the thoracic wall and the cardiac apex into the left or right ventricle. In case of the transvenous access, the right part of the heart with its valves is reached antegradely (i.e., with the bloodstream). After puncture of the atrial septum, also the left part of the heart can be reached. By the transarterial approach the left heart chambers and valves can be reached retrogradely.

WO 2004/047620 A2 describes a process of fixing tissue with a solution comprising a phenolic tannin. This international patent application further describes a process for replacing a damaged cardiac valve by implanting a bioprosthetic heart valve comprising fixed tissue comprising elastin cross-linked with a tannic acid cross-linking agent. The bioprostheses disclosed in this international patent application comprise, besides fixed tissue comprising elastin cross-linked with a tannic acid cross-linking agent, a support material attached to the fixed tissue.

WO 2004/113431 A1 relates to the use of a secoiridoid-containing substance as non-toxic cross-linking agent for the cross-linking of biopolymers, such as polypeptides polysaccharides.

WO 2006/115733 A2 relates to methods and products for the treatment of connective tissue weakened due to destruction of tissue architecture, in particular due to an elastin degradation. The treatment agents employ certain unique properties of phenolic compounds for a reduction of elastin degradation.

SUMMARY

It is an object of the present invention to provide methods and devices that facilitate the manufacture of cardiac valve prostheses that combine a long durability and a low disposition for the formation of thrombi on their surface.

This object is achieved by a method for manufacturing a cardiac valve prosthesis, wherein the method comprises the steps explained in the following.

First, human or animal body tissue is provided. Then, this human or animal body tissue is shaped outside the human or animal body in a shaping process. This shaping process aims in giving the body tissue the shape and size of a cardiac valve.

Afterwards, a fixation and stabilization of the body tissue by a cross-linking agent is carried out. In doing so, the shape given to the body tissue by the shaping process is preserved. Consequently, a stabilized cardiac valve prosthesis originating from the provided human or animal body tissue is obtained.

For carrying out the shaping and stabilization process, the body tissue is, in an embodiment, inserted into a cardiac valve mold and shaped by an appropriate shaping technique, e.g., by deep drawing. When the body tissue has adopted the desired form in the cardiac valve mold, the cross-linking agent is added to the shaped body tissue. The addition of the cross-linking agent results in cross-linking of the body tissue so that it stably remains in the shape that was given to the body tissue in the cardiac valve mold. An artificial cardiac valve, i.e. a cardiac valve prosthesis, results that is made from the body tissue. Due to chemical cross-linking of the body tissue, the shaped body tissue remains in its given shape even after removing the cross-linking agent and the mold. It is possible to implant the artificial cardiac valve to an individual.

In contrast to prior art techniques, according to which cross-linking agents are merely used to decrease the susceptibility of the used body tissue with respect to biodegradability, the method applied for manufacturing the claimed cardiac valve prosthesis makes use of a shaping process in which a desired shape and size, namely the shape and size of a cardiac valve, is given to the body tissue. The cross-linking agent then preserves this given shape. There is no indication in the prior art that a cross-linking agent could be used for preserving a given shape. Rather, to give an example, WO 2004/047620 A2 discloses a bioprosthesis that comprises on the one hand tissue fixed with a cross-linking agent but, on the on the hand, additionally a support material attached to the fixed tissue. Thus, the prior art teaches that the used cross-linking agents can be used for modifying the chemical structure of the treated body tissue. However, the prior art does not teach that a given shape of body tissue can be preserved by applying a cross-linking agent.

In contrast, the cardiac valve prosthesis according to the presently claimed invention is a self-contained cardiac valve prosthesis that does not need nor contains any further support material or support structures. Rather, it is free of additional support material or support structures. The cardiac valve prosthesis may be implanted in form of a cardiac valve prosthesis arrangement comprising the cardiac valve prosthesis and a carrier (e.g., a stent) connected to the cardiac valve prosthesis. For connecting the cardiac valve prosthesis to the carrier, the cardiac valve prosthesis can be sewn to the carrier. The carrier is, however, not necessary for structurally supporting the cardiac prosthesis. It rather serves for keeping the cardiac valve prosthesis in place in an implanted state and for allowing proper functioning of the cardiac valve prosthesis.

In an embodiment, the cross-linking agent comprises at least one or is a secoiridoid corresponding to the following general formula (I):

(I)

Thereby,
$R^1$ and $R^3$ denote independently of each other and independently of other residues in the compound H or $CH_3$,
$R^4$ denotes independently of other residues in the compound H or a residue having a structure according to general formula (II):

(II)

wherein
$R^5$, $R^6$, $R^7$, $R^8$, $R^9$ denote independently of each other and independently of other residues in the compound H or OH,
$R^2$ denotes independently of other residues in the compound H, OH or a residue having a structure according to general formula (III):

(III)

wherein
$R^{10}$, $R^{11}$, $R^{12}$, $R^{13}$ denote independently of each other and independently of other residues in the compound H or OH.

In case that $R^2$ corresponds to formula (III), the linkage between residue $R^2$ and the neighboring heterocycle of the compound is effected by the bond extending away from the oxygen atom of residue $R^2$ that is bound to the heterocycle of residue $R^2$ so that a structure of the following formula (VI) results:

(VI)

In an embodiment, the residues of the structure according to formula (I) have a conformation according to the following formula (IV):

(IV)

In an embodiment, the residue $R^2$ has a structure according to general formula (III) and has a conformation according to the following formula (V):

(V)

By a combination of the latter two embodiments, the following structure according to general formula (VII) results:

(VII)

In an embodiment, at least two of residues $R^5$, $R^6$, $R^7$, $R^8$, and $R^9$ denote OH.

In an embodiment, residues $R^5$, $R^6$, and $R^9$ denote H and residues $R^7$ and $R^8$ denote OH.

In an embodiment, residues $R^1$ and $R^3$ denote $CH_3$.

In an embodiment, residue $R^2$ denotes OH. Then, the cross-linking agent comprises or corresponds to the following general formulae (VIII) or (IX):

(VIII)

(IX)

In an embodiment, residues $R^1$ and $R^3$ denote $CH_3$ in formulae (VIII) and (IX).

In an embodiment, the cross-linking agent comprises a compound corresponding to the following formulae (X) or (XI) or corresponds itself to these formulae:

(X)

(XI)

A cross-linking agent having a structure corresponding to formula (X) is present in equilibrium with a structure corresponding to the following formula (XII):

(XII)

(XV)

A cross-linking agent having a structure corresponding to formula (XI) is present in equilibrium with a structure corresponding to the following formula (XIII):

(XIII)

(XVI)

In an embodiment, the cross linking agent comprises at least one compound or is a compound according to formula (VI), to formula (X), to formula (XI), to formula (XII), to formula (XIII) or a derivative thereof.

In an embodiment, the term "derivative" denotes a compound that can be derived by a naturally occurring biotransformation process from a specific compound. I.e., these derivatives would be formed within a human or animal body due to enzymatic activity or non-enzymatic biochemical transformation or maturation processes. Specific examples of derivatives of compounds according to formula (VI), to formula (X), to formula (XI), to formula (XII), or to formula (XIII) are compounds corresponding to the following formulae (XIV) to (XXII):

(XIV)

(XVII)

(XVIII)

(XIX)

(XX)

(XXI)

(XXII)

All of these derivatives, in particular compounds having a structure according to formulae (XI), (XIII), (XIX), (XX), (XXI), or (XXII) are particularly appropriate to cross-link human or animal body tissue.

Compounds that can be derived from the compound having a structure according to formula (I) in a similar biochemical way as the specific derivatives explained above are also encompassed by the presently claimed subject matter and form part of an aspect of the invention.

In an embodiment, at least two of residues $R^{10}$, $R^{11}$, $R^{12}$, $R^{13}$ denote OH.

In an embodiment, each of residues $R^{10}$, $R^{11}$, $R^{12}$, $R^{13}$ denotes OH.

In an embodiment, residues $R^5$, $R^6$, and $R^9$ denote H, residues $R^7$ and $R^8$ denote OH, residues $R^1$ and $R^3$ denote $CH_3$, residue $R^2$ corresponds to formula (III), and residues $R^{10}$, $R^{11}$, $R^{12}$, and $R^{13}$ denote OH. Then, the compound has a structure corresponding to the following general formula (XXIII):

(XXIII)

In an embodiment, residues $R^5$, $R^6$, and $R^9$ denote H, residues $R^7$ and $R^8$ denote OH, residues $R^1$ and $R^3$ denote $CH_3$, residue $R^2$ corresponds to formula (V), residues $R^{10}$, $R^{11}$, $R^{12}$, $R^{13}$ denote OH, and the residues of the structure according to formula (I) have a conformation according to formula (IV). Then, the compound has a structure corresponding to the following general formula (XXIV):

(XXIV)

In an embodiment, the cross-linking agent is used in a concentration of 0.01 to 10% (v/v) or (w/w), in particular of 0.02 to 9%, in particular of 0.03 to 8%, in particular of 0.04 to 7%, in particular of 0.05 to 6%, in particular of 0.06 to 5%, in particular of 0.07 to 4%, in particular of 0.08 to 3%, in particular of 0.09 to 2%, in particular of 0.1 to 1%, in particular of 0.2 to 0.9%, in particular of 0.3 to 0.8%, in particular of 0.4 to 0.7%, in particular of 0.5 to 0.6, with respect to the total amount of treatment solution.

In an embodiment, the cross-linking agent is kept in contact with the shaped body tissue over a time period lying in a range from 1 hour to 72 hours, in particular from 2 hours to 48 hours, in particular from 3 hours to 36 hours, in particular from 4 hours to 24 hours, in particular from 5 hours to 20 hours, in particular from 6 hours to 15 hours, in particular from 8 hours to 12 hours.

In an embodiment, the temperature is lying in a range of from 15° C. to 40° C., in particular from 20° C. to 38° C., in particular from 22° C. to 37° C., in particular from 25° C. to 35° C., in particular from 27° C. to 30° C. during an incubation of the shaped body tissue with the cross-linking agent.

In an embodiment, a treatment solution comprising the cross-linking agent also comprises a buffering agent that is capable of buffering the treatment solution around a pH value of approximately 5. A particular appropriate pH value of the treatment solution is a pH value lying in a pH range of from pH 4 to pH 6, in particular from pH 4.5 to pH 5.5, in particular from pH 4.7 to pH 5.2, in particular from pH 4.8 to pH 5.0. A citrate buffer is a particularly appropriate buffering agent.

In an embodiment, the shaped body tissue and the treatment solution are agitated on a shaker such as a rocking shaker during at least a part of the treatment of shaping process. To give an example, an agitation can be carried out over time period lying in a range of from 5 minutes to 2 hours, in particular of from 10 minutes to 1.5 hours, in particular of from 20 minutes to 1 hour, in particular of from 30 minutes to 45 minutes. The agitation is typically carried out at the beginning of the cross-linking process. An appropriate agitation speed is a speed lying in a range of from 10 rounds per minute (rpm) to 500 rpm, in particular of from 20 rpm to 450 rpm, in particular of from 30 rpm to 400 rpm, in particular of from 40 rpm to 350 rpm, in particular of from 50 rpm to 300 rpm, in particular of from 60 rpm to 250 rpm, in particular of from 70 rpm to 200 rpm, in particular of from 80 rpm to 150 rpm, in particular of from 90 rpm to 100 rpm.

In an embodiment, the shaping process is a deep drawing process. Such a deep drawing process is particularly appropriate for giving the desired shape to the body tissue.

In an embodiment, a mold for an individually personalized cardiac valve prosthesis is used in the shaping process. Such a mold facilitates the shaping of the body tissue and ensures that the body tissue in fact obtains the desired shape and size. The mold can be individually manufactured according to the personal needs of a recipient of the cardiac valve prosthesis. This will be explained in the following in more detail.

In an embodiment, the mold for an individually personalized cardiac valve prosthesis is manufactured by a method comprising the steps explained in the following.

First, 3-D imaging data of an impaired cardiac valve of an individual is provided or obtained. The 3-D imaging data can be provided in form of the dataset. Then, this 3-D imaging data has been obtained by an appropriate imaging method prior to carrying out the claimed method. Alternatively, the 3-D imaging data can be obtained by an appropriate imaging method while carrying out the method for manufacturing the cardiac valve prosthesis. Appropriate imaging methods are, e.g., magnetic resonance imaging (MRI), computed tomography (CT), (3-D) ultrasound (e.g., echocardiography), or 3-D rotational angiography.

Afterwards, the 3-D imaging data is reconstructed in a three-dimensional manner. Thereby, impairments of the impaired cardiac valve are at least partially corrected (so-called virtual valve surgery). As a result, reconstructed 3-D imaging data is obtained that represents a virtual cardiac valve. This virtual cardiac valve has a performance that better corresponds to the performance of a non-impaired cardiac valve than the performance of the impaired cardiac valve does. The term "performance" is in particular to be understood as the ability to open and close in a cardiac blood vessel or heart chamber. Thus, the cardiac valve having a good performance has a good ability to open and close in a cardiac blood vessel or heart chamber.

Subsequently, the reconstructed 3-D imaging data is used to generate a virtual 3-D mold for a cardiac valve prosthesis. Since the reconstructed 3-D imaging data is based on imaging data of a specific individual, the virtual 3-D mold is a mold for an individually personalized cardiac valve prosthesis.

Finally, the virtual 3-D mold is used to manufacture a real mold for a cardiac valve prosthesis. To be more precise, it is used to manufacture a real mold for an individually personalized cardiac valve prosthesis.

This real mold for an individually personalized cardiac valve prosthesis is then used to manufacture an individually personalized cardiac valve prosthesis. This can be done, e.g., by applying the body tissue into the real mold and to give the inserted body tissue the shape of the real mold, e.g., by applying positive or negative pressure, suction or vacuum, temperature changes.

In an embodiment, the performance of the virtual cardiac valve that is represented by the reconstructed 3-D imaging data is tested by simulation after the step of 3-D reconstructing the 3-D imaging data. This simulation is done in terms of systolic and diastolic flow and/or vortices and/or streamlines and/or pressure fields and/or a pressure gradient across the virtual cardiac valve. By such a simulation, the performance of the virtual cardiac valve can be assessed in more detail in order to ensure that the virtual cardiac valve has indeed a better performance than the impaired cardiac valve that is to be replaced. The simulation of the performance of the virtual cardiac valve can best be done by specialized software.

In an embodiment, the 3-D imaging data is the 3-D imaging data of an impaired human cardiac valve.

In an embodiment, the 3-D imaging data is the 3-D imaging data of an impaired animal valve. The animal is, in an embodiment, a rodent or a non-human mammal.

In an embodiment, the step of 3-D reconstruction of the 3-D imaging data comprises a step in which at least one impaired or diseased area of the impaired cardiac valve is virtually excised (so-called virtual valve surgery). Furthermore, the excised area is then replaced by a remodeled area having an appearance of healthy tissue, in particular of healthy cardiac tissue. Then, the reconstructed 3-D imaging data resembles or corresponds to a non-impaired cardiac valve.

While it is generally possible to manufacture the real mold for an individually personalized cardiac valve prosthesis by any appropriate manufacturing method, this step is done, in an embodiment, by injection molding or by 3-D printing. 3-D printing is particular appropriate since it allows for manufacturing individually personalized molds at particularly low cost and high speed.

The real mold for an individually personalized cardiac valve prosthesis can be used to manufacture any kind of cardiac valve prosthesis. Hence, it is, in an embodiment, a mold for an aortic valve prosthesis. In another embodiment, it is a mold for a pulmonary valve prosthesis. In another embodiment, it is a mold for a mitral valve prosthesis. In another embodiment, it is a mold for a tricuspid valve prosthesis.

In an embodiment, the body tissue to be shaped is connective tissue, fascial tissue, peritoneal tissue or cardiac tissue.

In an embodiment, the body tissue, the given shape of which is to be preserved, is cardiac muscle tissue. In an embodiment, the body tissue to be shaped is pericardial tissue (pericardium).

In an embodiment, the body tissue is excised or harvested from an individual who will also be the recipient of the manufactured cardiac valve prosthesis prior to performing the shaping process. In doing so, it is possible to produce an autogenic (autologous) cardiac valve prosthesis. If this embodiment is combined with the embodiments relating to manufacturing a mold for an individually personalized cardiac valve prosthesis, it is possible to produce an individually personalized autogenic cardiac valve prosthesis.

In an aspect, the present invention relates to a cardiac valve prosthesis that is or can be manufactured with a method according to the preceding explanations.

In an aspect, the present invention relates to a method of implanting a cardiac valve prosthesis to an individual in need thereof. This method comprises the steps explained the following.

In a first step, body tissue is excised or harvested from a donor. The donor can be a human or animal patient.

Afterwards, the body tissue is shaped in a shaping process to give the body tissue a shape and size of a cardiac valve of a recipient. Once again, the recipient can be a human or animal patient.

Afterwards, the body tissue is subjected to a fixation and stabilization process. This process is done with the help of a cross-linking agent. The fixation and stabilization preserve the shape given to the body tissue in the shaping process. Consequently, a cardiac valve prosthesis is obtained.

Afterwards, the cardiac valve prosthesis is implanted into the recipient.

In an embodiment, the recipient is different from the donor. If both the recipient and the donor are a human or an animal of the same species, an allogeneic (homologous) cardiac valve prosthesis can be produced and implanted.

In an embodiment, the recipient is identical to the donor. In such a case, an autogenic cardiac valve prosthesis is produced and implanted.

In an embodiment, the cardiac valve prosthesis is an aortic valve prosthesis. In another embodiment, the cardiac valve prosthesis is a pulmonary valve prosthesis. In another embodiment, the cardiac valve prosthesis is a mitral valve prosthesis. In another embodiment, the cardiac valve prosthesis is a tricuspid valve prosthesis.

In an embodiment, the body tissue to be shaped is connective tissue, fascial tissue, peritoneal tissue or cardiac tissue. In an embodiment, the body tissue to be shaped is pericardial tissue (pericardium).

In an embodiment, the diameter of the cardiac valve prosthesis obtained after the fixation and stabilization step has an oversizing of 10% to 50%, in particular of 12% to 45%, in particular of 15% to 40%, in particular of 20% to 35%, in particular of 25% to 30% with respect to a diameter of a blood vessel into which the cardiac valve prosthesis is to be implanted. Thus, in this embodiment, the cardiac valve prosthesis is made bigger as the available physiologic space within the blood vessel in which the cardiac valve prosthesis is intended to regulate blood flow. Such an oversizing facilitates a proper sealing of the cardiac valve prosthesis against the blood vessel into which the cardiac valve prosthesis is implanted so that the functionality of the cardiac valve prosthesis is increased. In particular, a temporal interruption of blood flow (closed state of the cardiac valve prosthesis) during a cardiac cycle can be better achieved when applying such oversizing.

In an embodiment, the cardiac valve prosthesis obtained after the fixation and stabilization process is sewed into a supporting structure prior to implanting it. Such a supporting structure can, e.g., be a stent structure (often also denoted as frame or carrier). The supporting structure can be made from a self-expanding metal such as Nitinol. By using such a supporting structure together with the cardiac valve prosthesis, a particularly easy implantable cardiac valve prosthesis assembly can be provided.

In an embodiment, the diameter of the cardiac valve prosthesis assembly comprising the cardiac valve prosthesis and the supporting structure to which the cardiac valve prosthesis is sewed has an oversizing of 10% to 50%%, in particular of 12% to 45%, in particular of 15% to 40%, in particular of 20% to 35%, in particular of 25% to 30% with respect to a diameter of a blood vessel into which the cardiac valve prosthesis is to be implanted. Thus, in this embodiment, the cardiac valve prosthesis assembly is made bigger as the available physiologic space within the blood vessel in which the cardiac valve prosthesis assembly is intended to regulate blood flow. Such an oversizing facilitates a proper sealing of the cardiac valve prosthesis assembly against the blood vessel into which the cardiac valve prosthesis assembly is implanted so that the functionality of the cardiac valve prosthesis assembly is increased. In particular, a temporal interruption of blood flow (closed state of the cardiac valve prosthesis) during a cardiac cycle can be better achieved when applying such oversizing.

In an embodiment, the cardiac valve prosthesis is implanted into a blood vessel of the recipient by a transcatheter method, by a minimally invasive procedure, by a hybrid procedure combining catheter and surgical techniques or by a surgical method. All of these methods are likewise appropriate to implant the cardiac valve prosthesis.

In an embodiment, a mold for an individually personalized cardiac valve prosthesis is used in the shaping process to give the body tissue desired shape. Such a mold for an individually personalized cardiac valve prosthesis is manufactured by a method comprising the steps explained in the following.

First, 3-D imaging data of an impaired cardiac valve of an individual is provided or obtained. The 3-D imaging data can be provided in form of the dataset. Then, this 3-D imaging data has been obtained by an appropriate imaging method prior to carrying out the claimed method. Alternatively, the 3-D imaging data can be obtained by an appropriate imaging method while carrying out the method of implanting a cardiac valve prosthesis. Appropriate imaging methods are, e.g., cardiac magnetic resonance imaging, computed tomography, echocardiography, and 3-D rotational angiography.

Afterwards, the 3-D imaging data is reconstructed in a three-dimensional manner. Thereby, impairments of the impaired cardiac valve are at least partially corrected (so-called virtual valve surgery). As a result, reconstructed 3-D imaging data is obtained that represents a virtual cardiac valve. This virtual cardiac valve has a performance that better corresponds to the performance of a non-impaired cardiac valve than the performance of the impaired cardiac valve does. The term "performance" is in particular to be understood as the ability to open and close in a cardiac blood vessel or heart chamber. Thus, the cardiac valve having a good performance has a good ability to open and close in a cardiac blood vessel or heart chamber.

Subsequently, the reconstructed 3-D imaging data is used to generate a virtual 3-D mold for a cardiac valve prosthesis. Since the reconstructed 3-D imaging data is based on imaging data of a specific individual, the virtual 3-D mold is a mold for an individually personalized cardiac valve prosthesis.

Finally, the virtual 3-D mold is used to manufacture a real mold for a cardiac valve prosthesis. To be more precise, it is used to manufacture a real mold for an individually personalized cardiac valve prosthesis.

This real mold for an individually personalized cardiac valve prosthesis is then used to manufacture an individually personalized cardiac valve prosthesis.

In an aspect, the present invention also relates to a (non-transitory) computer program product comprising a software with executable code that causes a computer to perform the steps explained in the following upon being executed on the computer. First, provided 3-D imaging data of an impaired cardiac valve of an individual is automatically 3-D reconstructed. Thereby, impairments of the impaired cardiac valve are at least partially corrected. This results in reconstructed 3-D imaging data representing a virtual cardiac valve having a performance that better corresponds to the performance of a non-impaired cardiac valve than the performance of the impaired cardiac valve does.

Furthermore, the computer program causes the computer to automatically use the reconstructed 3-D imaging data to generate a virtual 3-D mold for a cardiac valve prosthesis.

In an embodiment, the software causes the computer additionally to automatically control the manufacturing of a real mold for an individually personalized cardiac prosthesis on the basis of the virtual 3-D mold. Thus, the computer program can control, e.g., a 3-D printer to manufacture a real mold for an individually personalized cardiac valve prosthesis.

In an embodiment, the software causes the computer to perform an additional step prior to automatically generating a virtual 3-D mold for a cardiac valve prosthesis, namely a step of simulating the performance of the virtual cardiac valve in terms of systolic and diastolic flow and/or vortices and/or streamlines and/or pressure fields and/or a pressure gradient across the virtual cardiac valve.

In an aspect, the invention also relates to a mold for an individually personalized cardiac valve prosthesis that is or can be obtained by a method according to the preceding explanations.

In an aspect, the present invention relates to a medical method of treating a cardiac disease resulting from impaired cardiac valve by replacing an impaired or diseased cardiac valve of a human or animal in need thereof by a cardiac valve prosthesis according to the preceding explanations.

In an aspect, the present invention relates to the medical use of a cardiac valve prosthesis according to the preceding explanations in therapy of a cardiac disease resulting from an impaired cardiac valve. Such a cardiac disease can be, e.g., a cardiac valve insufficiency or a stenosis.

All embodiments of the described methods can be combined in any desired way and can be transferred either individually or in any arbitrary combination to another of the described methods, to the described cardiac valve prosthesis, to the described computer program product and to the described mold for an individually personalized cardiac valve prosthesis, and vice versa.

BRIEF DESCRIPTION OF THE FIGURES

Further details of aspects of the present invention will be explained in the following with respect to exemplary embodiments and accompanying Figures. In the Figures.

DETAILED DESCRIPTION

Figures 1, 2:
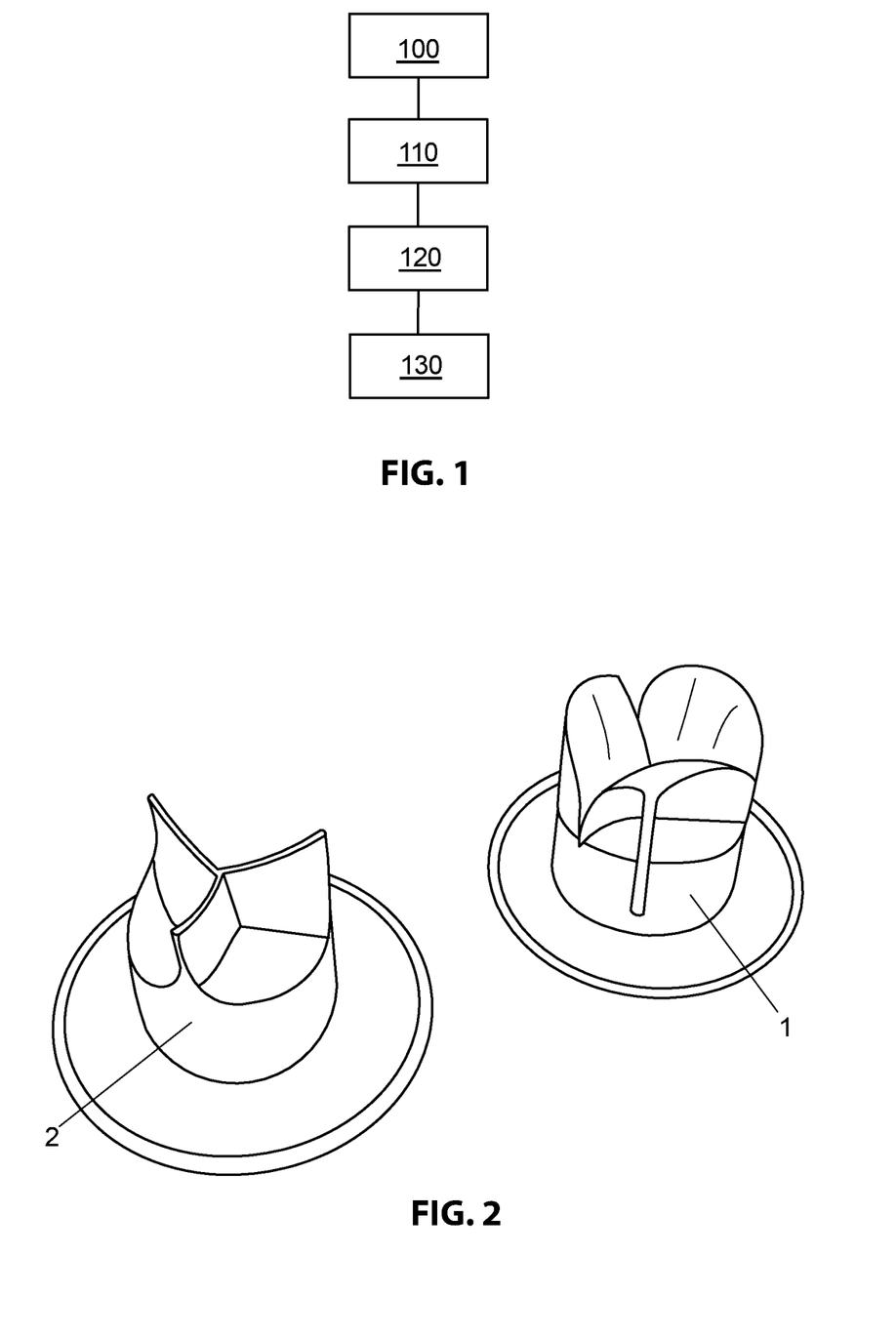
FIG. 1 shows a flowchart of a method for manufacturing a mold for a cardiac valve prosthesis.
FIG. 2 shows an exemplary embodiment of such a mold.

FIG. 1 shows a flowchart of an exemplary embodiment of a method for manufacturing a mold for a cardiac valve prosthesis. In a first step 100, 3-D imaging data of an impaired human cardiac valve is provided.

In a second step 110, the 3-D imaging data is reconstructed. This second step 110 can also be denoted as virtual cardiac valve surgery. By this step, a detected impairment of the human cardiac valve from which the 3-D imaging data was obtained is virtually corrected. This impairment typically results in a more or less pronounced dysfunction of the human cardiac valve. When performing the virtual cardiac valve surgery 110, the according impairment is virtually correct. Thus, reconstructed 3-D imaging data results that represents a human cardiac valve having better functional properties than the human cardiac valve from which the 3-D imaging data was obtained. Expressed in other words, the cardiac valve of the reconstructed 3-D imaging data has a better functionality than the original cardiac valve from which the 3-D imaging data has been obtained.

In a third step 120, the reconstructed 3-D imaging data is used for generating a virtual 3-D mold for a personalized cardiac valve prosthesis.

Subsequently, the virtual 3-D mold is used in a fourth step 130 to manufacture a real mold for a cardiac valve prosthesis. This real mold will then serve for manufacturing a cardiac valve prosthesis having better properties than the cardiac valve from which the 3-D imaging data has been obtained.

FIG. 2 shows an exemplary embodiment of a mold for manufacturing a cardiac valve prosthesis. This mold comprises a first part 1 and a second part 2 that can be fit into each other. The first part 1 and the second part 2 act together as negative and positive form of a cardiac valve prosthesis to be manufactured.

Figure 3:
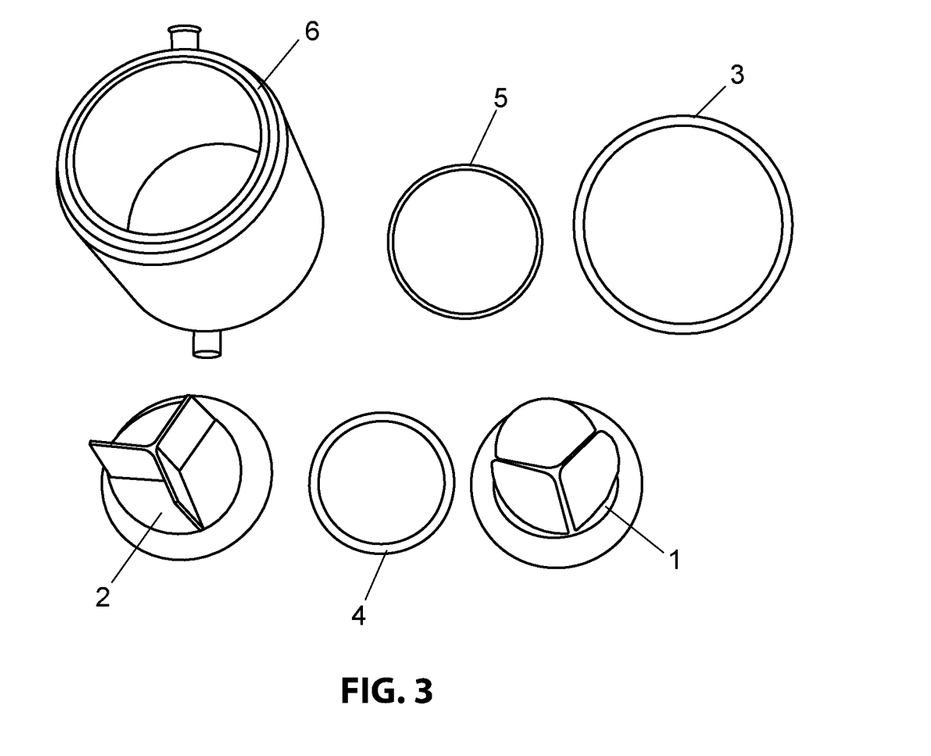
FIG. 3 shows the mold of FIG. 2 with further components.

FIG. 3 shows the first part 1 and the second part 2 of the mold depicted in FIG. 2 with further components, namely a plate 3, a ring 4, a gasket 5 and a reaction container 6. These components are typically provided in a set. It is possible to assemble the first part 1 and the second part 2 of the mold after having placed cardiac tissue between them. This cardiac tissue is then hold in place by the ring 4. Afterwards, the assembly of the first part 1, the second part 2, the cardiac tissue and a gasket 5 can be placed into the reaction container 6. The plate 3 serves for assisting in manipulation steps during proper placement of cardiac tissue between the first part 1 and the second part 2 of the mold.

The individual steps of manufacturing a cardiac valve prosthesis with the help of the first part 1 and the second part 2 of the mold will be explained in the following in more detail making reference to FIGS. 4 to 8. The same numeral references will be used in all Figures for explaining the same or similar elements.

Figure 4:
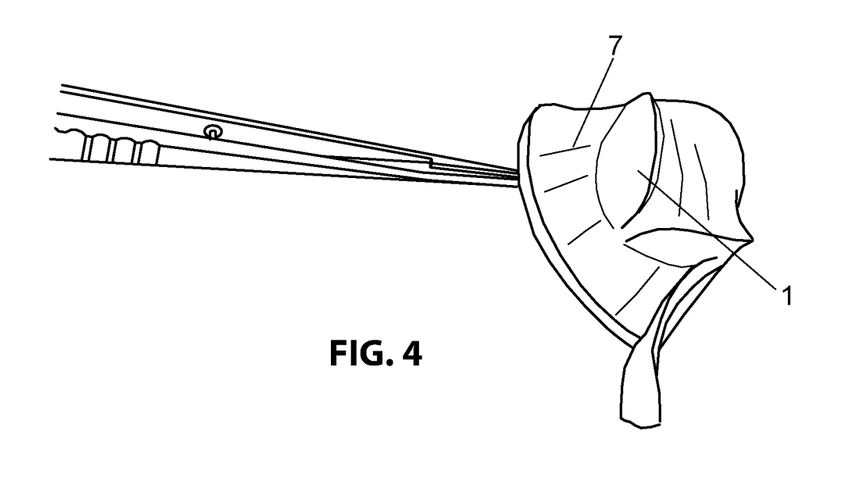
FIG. 4 shows a first step of an application method of the mold of FIG. 2.

As shown in FIG. 4, pericardium 7 or other cardiac tissue is tightly drawn above the first part 1 of the mold. This is done with the help of a pair of tweezers 8. However, other manipulation instruments can also be used.

Figure 5:
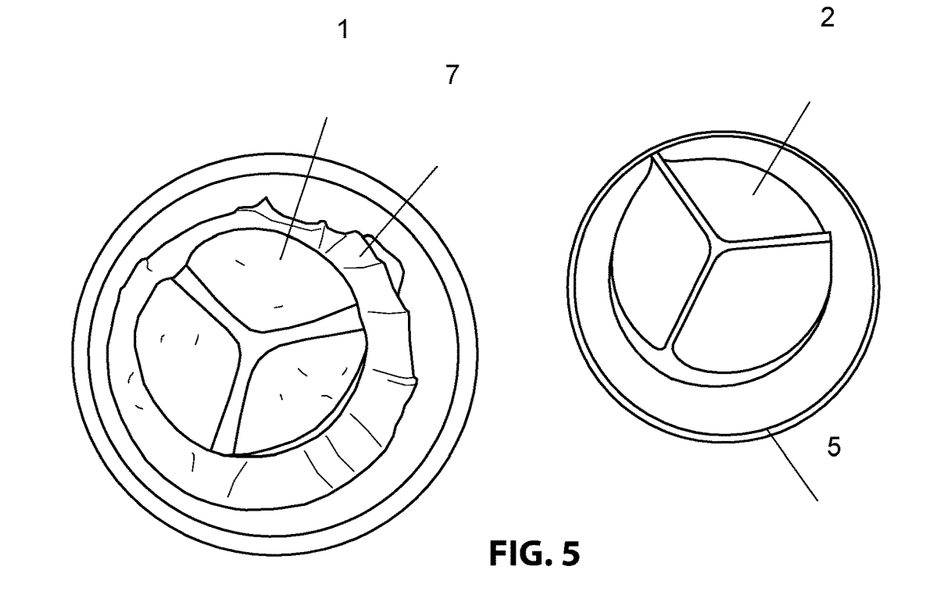
FIG. 5 shows a second step of an application method of the mold of FIG. 2.

As shown in a top view in FIG. 5, the pericardium 7 then fully covers the first part 1 of the mold. In contrast, the second part 2 of the mold is not yet covered with pericardium. However, the gasket 5 is already placed around the first part 1 of the mold.

Figure 6:
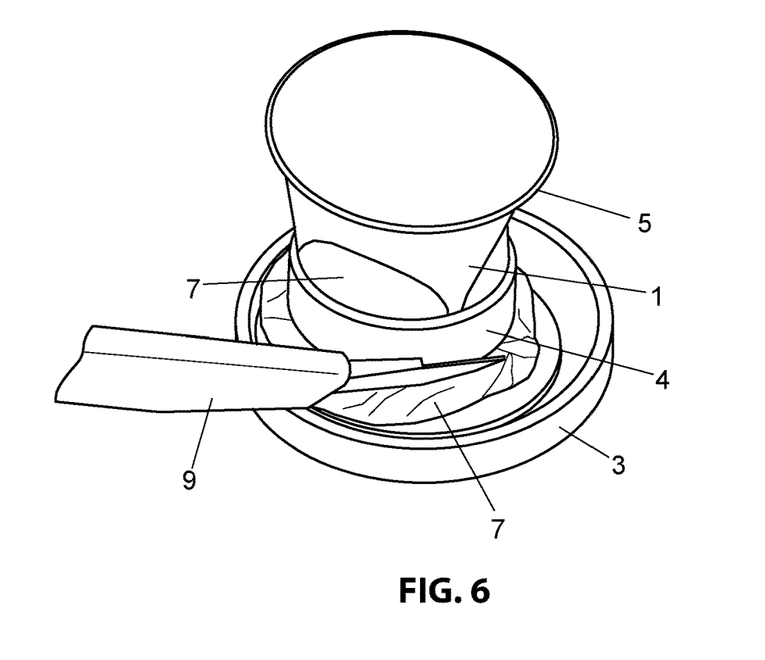
FIG. 6 shows a third step of an application method of the mold of FIG. 2.

As shown in FIG. 6, the second part 2 is then placed above the first part 1 of the mold, wherein the pericardium 7 is pressed between the first part 1 and the second part 2 of the mold. Furthermore, the ring 4 serves for keeping the pericardium 7 in place. Pericardium 7 protruding from the second part 2 of the mold and from the ring 4 is cut with a scalpel 9. This is done on the plate 3 providing a clean and plane cutting surface.

Figure 7:
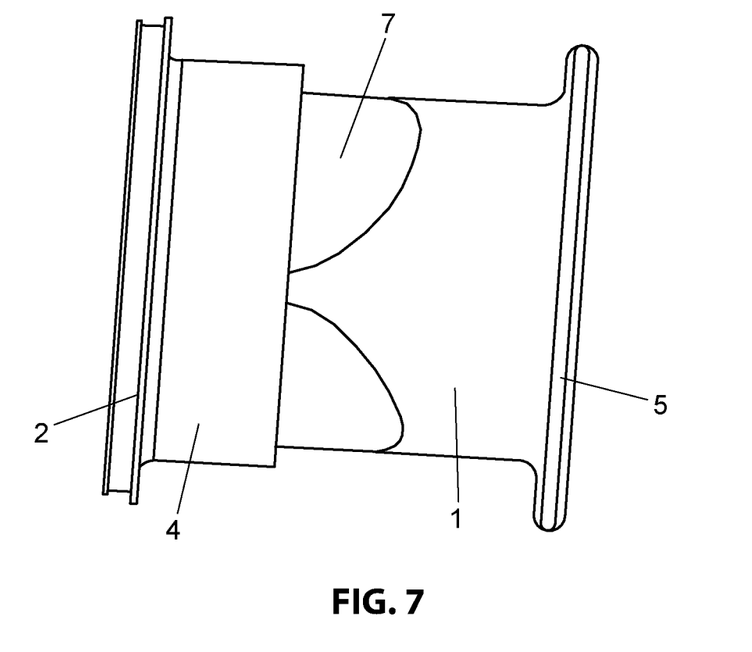
FIG. 7 shows a fourth step of an application method of the mold of FIG. 2.
Figure 8:
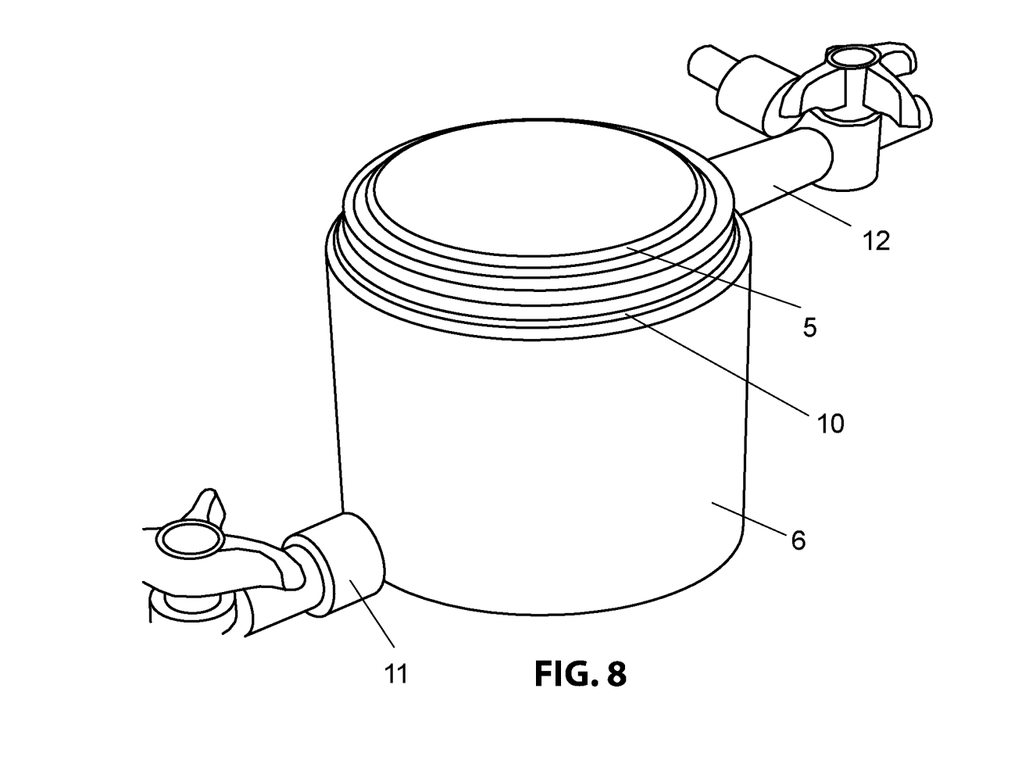
FIG. 8 shows a fifth step of an application method of the mold of FIG. 2.

FIG. 7 shows the fully assembled mold with the first part 1 of the mold overlaying the second part 2 of the mold and the ring 4 securing the pericardium 7 on the mold. This fully assembled mold can then be placed into the reaction container 6, as shown in FIG. 8. A lid (e.g., the plate 3 shown in FIG. 3) can be placed on top of the reaction container 6. The gasket 5 and a reaction container gasket 10 will then serve for a sufficient sealing between an interior of the reaction container 6 and an exterior.

The reaction container 6 comprises an inlet port 11 and an outlet port 12. A reaction liquid can be fed into the reaction container 6 through the inlet port 11 and can be drained from an interior of the reaction container 6 by the outlet 12.

In the embodiment shown in FIG. 8, a reaction liquid comprising a cross-linker is fed into the interior of the reaction container 6. This cross-linker serves for cross-linking the pericardium 7 so as to keep it in the form given to the pericardium 7 by the mold. Thus, when releasing the first part 1 of the mold from the second part 2 of the mold, the pericardium 7 still retains the shape that has been given to it by the first part 1 of the mold and the second part 2 of the mold, i.e. the shape of a cardiac valve. After separation of the leaflets, the shaped pericardium 7 can subsequently be used as fully functional cardiac valve prosthesis.

To identify whether different cross-linking agents might have a different effect on the cross-linking of body tissue, in vitro tests were performed. For this purpose, human and animal body tissue was used and shaped in a deep-drawing process to give the body tissue the shape and size of a cardiac valve, namely of a pulmonary artery valve.

Afterwards, the shaped body tissue was fixated and stabilized by the addition of two different cross-linking agents. On the one hand, glutaraldehyde (GA) was used, on the other hand a compound having the structure of formula (X) was used. The latter compound will be referred to as compound X in the following. The final concentration of GA was chosen to be in a range of 0.2 to 0.625% in the treatment solution. The final concentration of compound X was chosen to be 0.05% in the treatment solution. The incubation was carried out over time period of 20 minutes (GA) or 24 hours (compound X) at a temperature lying in a range of 20° C. to 40 C. The treatment solution containing the cross-linking agent was buffered by a citrate buffer in a pH range of pH 4.8 to pH 5.0. Within the first 30 minutes of the cross-linking process, the shaped body tissue and the treatment solution were agitated by a rocking shaker at 100 rpm.

Afterwards, a tensile test was carried out. While both GA and compound X were generally able to cross-link the shaped body tissue, it turned out that compound X was even more appropriate for the cross-linking process since it resulted in a more stable structure of the shaped body tissue.

Figure 9:
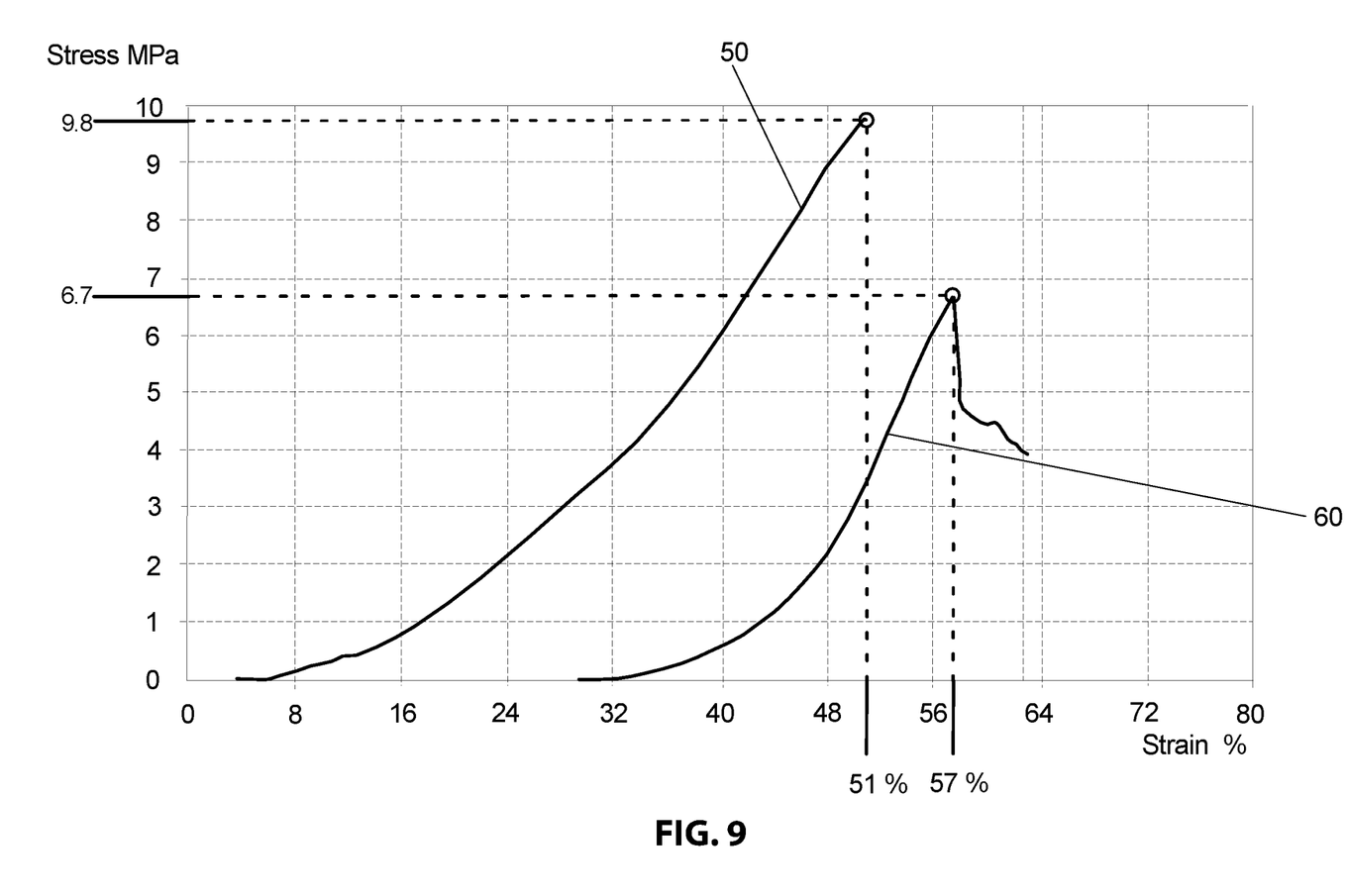
FIG. 9 shows a comparison between two possible cross-linking agents used for cross-linking shaped body tissue.

As can be seen from FIG. 9, the body tissue treated with compound X (curve 50) showed a 1.5-fold higher stress resistance than the body tissue cross-linked with GA (curve 60) (9.5 MPa vs. 6.7 MPa). At the same time, the maximum achieved strain was 10% higher in case of the cross-linking with GA than in case of compound X (57% vs. 51%). For the functioning of a cardiac valve, however, a higher stress resistance and a sufficiently high strain resistance is believed to be more important than a high strain resistance alone. Therefore, it was decided to carry out subsequent characterization tests only with respect to the shaped body tissue cross-linked with compound X.

An investigation of the shrinking temperature by differential scanning calorimetry (DSC) showed that the body tissue was sufficiently cross-linked. Subsequent cytotoxicity and biocompatibility tests showed no relevant cytotoxicity and sufficiently high biocompatibility. When placing the cross-linked body tissue into a fibroblast culture, no necroses could be observed.

Afterwards, in vivo tests were performed to evaluate the stability of the cross-linked body tissue over an extended period of time under real conditions.

In a first preclinical study, the general feasibility and safety of the heart valve replacement method was successfully shown.

In a second preclinical study, the long-term stability of the manufactured cardiac valve prosthesis was examined. A sufficiently high stabilization of the cross-linked tissue over a time period of 1.5 years was shown in an animal model (sheep). No cardiac insufficiency with more than 20% regurgitation fraction was observed. Furthermore, no cardiac valve stenosis could be observed.

The manufactured cardiac valve prosthesis was also subjected to different histologic examinations. The thickness, length, and structure of the manufactured valve prosthesis corresponded to the thickness, length and structure of the replaced natural heart valve. No thrombi could be observed in general and in the hinge region of the cusps. A full and correctly localized re-endothelialization was observed for the heart valve prosthesis. A correctly localized formation of neointima to a full extent could be observed.

Upon analyzing a foreign body response as well as other inflammation responses with a focus on M1 (CD80), M2 (CD163) macrophages, T cells (CD3), B cells (CD79a), an increased amount of M2 macrophages was observed. This can be taken as an indication of an immune response with desired subsequent differentiation to myofibroblasts.

No relevant neovascularization could be observed. The cardiac valve prosthesis showed full apposition onto the pulmonary arterial wall. No calcification could be observed. Furthermore, no indicators of necroses of the native pulmonary arterial wall could be seen.

Summarizing, the cardiac valve prosthesis manufactured by shaping body tissue and cross-linking it with cross-linking compound X resulted in a fully functional cardiac prosthesis that was properly integrated into the native surrounding body tissue and that remained stable over an extended period of time.

The invention claimed is:

1. A method for manufacturing a cardiac valve prosthesis, the method comprising the following steps:
   a) shaping human or animal body tissue in a shaping process to give the body tissue a shape and size of a cardiac valve, and
   b) fixation and stabilization of the body tissue by a cross-linking agent, thereby preserving the shape given to the body tissue by the shaping process and thus obtaining a cardiac valve prosthesis,
   wherein the body tissue is excised or harvested from an individual who is also an intended recipient of the manufactured cardiac valve prosthesis prior to performing the shaping process, and
   wherein a diameter of the obtained cardiac valve prosthesis has an oversizing of 10 to 50 % with respect to a diameter of a blood vessel to be treated by the cardiac valve prosthesis when implanted.

2. The method of claim 1, wherein the shaping process is a deep drawing process.

3. The method of claim 1, wherein a mold for an individually personalized cardiac valve prosthesis is used in the shaping process to give the body tissue the desired shape.

4. The method of claim 3, wherein the mold for an individually personalized cardiac valve prosthesis is manufactured by a method comprising the following steps:
   a) providing or obtaining 3-D imaging data of an impaired cardiac valve of an individual by an appropriate imaging method,
   b) 3-D reconstructing the 3-D imaging data, thereby at least partially correcting impairments of the impaired cardiac valve so as to obtain reconstructed 3-D imaging data representing a virtual cardiac valve having a performance that better corresponds to the performance of a non-impaired cardiac valve than the performance of the impaired cardiac valve does,
   c) using the reconstructed 3-D imaging data to generate a virtual 3-D mold for an individually personalized cardiac valve prosthesis, and
   d) using the virtual 3-D mold to manufacture a real mold for an individually personalized cardiac valve prosthesis.

5. The method of claim 4, wherein 3-D reconstructing the 3-D imaging data comprises virtually excising at least one impaired or diseased area of the impaired cardiac valve and remodeling the excised area to have an appearance of healthy tissue.

6. The method of claim 1, wherein the cardiac valve prosthesis is at least one of an aortic valve prosthesis, a pulmonary valve prosthesis, a mitral valve prosthesis, and a tricuspid valve prosthesis.

7. The method of claim 1, wherein the body tissue to be shaped is connective tissue, fascial tissue, peritoneal tissue or cardiac tissue.

8. The method of claim 1, wherein the body tissue to be shaped is pericardial tissue.

9. A cardiac valve prosthesis, obtainable by a method according to claim 1.

10. A method of implanting a cardiac valve prosthesis to an individual in need thereof, the method comprising the following steps:
    a) excising or harvesting body tissue from a donor,
    b) shaping the body tissue in a shaping process to give the body tissue a shape and size of a cardiac valve of a recipient,
    c) fixation and stabilization of the body tissue by a cross-linking agent, thereby preserving the shape given to the body tissue by the shaping process and thus obtaining a cardiac valve prosthesis, and
    d) implanting the cardiac valve prosthesis to the recipient,
    wherein a mold for an individually personalized cardiac valve prosthesis is used in the shaping process to give the body tissue the desired shape,
wherein the mold for an individually personalized cardiac valve prosthesis is manufactured by a method comprising the following steps:
    b1) providing or obtaining 3-D imaging data of an impaired cardiac valve of an individual by an appropriate imaging method,
    b2) 3-D reconstructing the 3-D imaging data, thereby at least partially correcting impairments of the impaired cardiac valve so as to obtain reconstructed 3-D imaging data representing a virtual cardiac valve having a performance that better corresponds to the performance of a non-impaired cardiac valve than the performance of the impaired cardiac valve does,
    b3) using the reconstructed 3-D imaging data to generate a virtual 3-D mold for an individually personalized cardiac valve prosthesis, and
    b4) using the virtual 3-D mold to manufacture a real mold for an individually personalized cardiac valve prosthesis, and
wherein a diameter of the obtained cardiac valve prosthesis has an oversizing of 10 to 50 % with respect to a diameter of a blood vessel to be treated by the cardiac valve prosthesis when implanted.

11. The method of claim 10, wherein the recipient is identical to the donor.

12. The method of claim 10, wherein the cardiac valve prosthesis is at least one of an aortic valve prosthesis, a pulmonary valve prosthesis, a mitral valve prosthesis, and a tricuspid valve prosthesis.

13. The method of claim 10, wherein the body tissue to be shaped is connective tissue, fascial tissue, peritoneal tissue or cardiac tissue.

14. The method of claim 10, wherein the cardiac valve prosthesis obtained in step c) is sewed in a supporting structure prior to implanting it.

15. The method of claim 14, wherein a diameter of the cardiac valve prosthesis that is sewed in the supporting structure has an oversizing of 10 to 50% with respect to a diameter of a blood vessel to be treated by the cardiac valve prosthesis when implanted.

16. The method of claim 10, wherein the cardiac valve prosthesis is implanted by a trans-catheter method, by a minimally invasive procedure, by a hybrid procedure combining catheter and surgical techniques, or by surgical method.

17. A method of implanting a cardiac valve prosthesis to an individual in need thereof, the method comprising the following steps:
   a) excising or harvesting body tissue from a donor,
   b) shaping the body tissue in a shaping process to give the body tissue a shape and size of a cardiac valve of a recipient,
   c) fixation and stabilization of the body tissue by a cross-linking agent, thereby preserving the shape given to the body tissue by the shaping process and thus obtaining a cardiac valve prosthesis, and
   d) implanting the cardiac valve prosthesis to the recipient, wherein the cardiac valve prosthesis obtained in step c) is sewed in a supporting structure prior to implanting it, and wherein a diameter of the cardiac valve prosthesis obtained in step c) has an oversizing of 10 to 50 % with respect to a diameter of a blood vessel to be treated by the cardiac valve prosthesis when implanted.

18. The method of claim 17, wherein the recipient is identical to the donor.

19. The method of claim 17, wherein the cardiac valve prosthesis is at least one of an aortic valve prosthesis, a pulmonary valve prosthesis, a mitral valve prosthesis, and a tricuspid valve prosthesis.

20. The method of claim 17, wherein the body tissue to be shaped is connective tissue, fascial tissue, peritoneal tissue, or cardiac tissue.

21. The method of claim 17, wherein a diameter of the cardiac valve prosthesis that is sewed in the supporting structure has an oversizing of 10 to 50% with respect to a diameter of a blood vessel to be treated by the cardiac valve prosthesis when implanted.

22. The method of claim 17, wherein the cardiac valve prosthesis is implanted by a trans-catheter method, by a minimally invasive procedure, by a hybrid procedure combining catheter and surgical techniques, or by surgical method.

23. The method of claim 17, wherein a mold for an individually personalized cardiac valve prosthesis is used in the shaping process to give the body tissue the desired shape.

* * * * *